United States Patent [19]

Garcia-Golding et al.

[11] Patent Number: 5,260,667
[45] Date of Patent: Nov. 9, 1993

[54] METHOD AND APPARATUS FOR DETERMINING THE PERCENTAGE WATER CONDENT OF OIL IN WATER EMULSION BY SPECIFIC ADMITTANCE MEASUREMENT

[75] Inventors: Fernando Garcia-Golding; Mario Giallorenzo; Noel Moreno; Cesar Alvarez; Victor Chang, all of Caracas, Venezuela

[73] Assignee: Intevep, S.A., Caracas, Venezuela

[21] Appl. No.: 801,475

[22] Filed: Dec. 2, 1991

[51] Int. Cl.[5] .................. G01R 27/22; G01N 27/06
[52] U.S. Cl. .................. 324/694; 324/698; 324/717; 324/721; 73/61.44
[58] Field of Search ............... 324/691, 693, 694, 696, 324/698, 705, 717, 721; 73/53.05, 61.43, 61.44

[56] References Cited

U.S. PATENT DOCUMENTS

| | | | |
|---|---|---|---|
| 4,112,744 | 9/1978 | Tassano | 73/61.43 X |
| 4,774,680 | 9/1988 | Agar | 324/698 X |
| 4,801,863 | 1/1989 | Schimion et al. | 324/698 X |
| 5,033,289 | 7/1991 | Cox | 324/689 X |

Primary Examiner—Gerard R. Strecker
Assistant Examiner—Diep Do
Attorney, Agent, or Firm—Bachman & LaPointe

[57] ABSTRACT

An apparatus and a method for determining the water content of an oil-in-water emulsion is disclosed. The apparatus includes a first sensor for measuring the real part of specific admittance of the emulsion, a second sensor which acts as a temperature compensation device and electronic circuitry for producing a signal representative of the water content of the emulsion. The method for determining the water content comprises measuring the real part of specific admittance of an oil-in-water emulsion and providing a signal representative thereof, providing a reference signal indicative of the emulsion temperature, adjusting the measured real part of specific admittance signal with the reference signal and converting the adjusted signal into a current signal representative of the percentage water content of the emulsion.

14 Claims, 5 Drawing Sheets

SIGNAL PROCESSOR

DETAILS FOR ADMITTANCE CONDITIONER AND SYNCHRONOUS DETECTOR

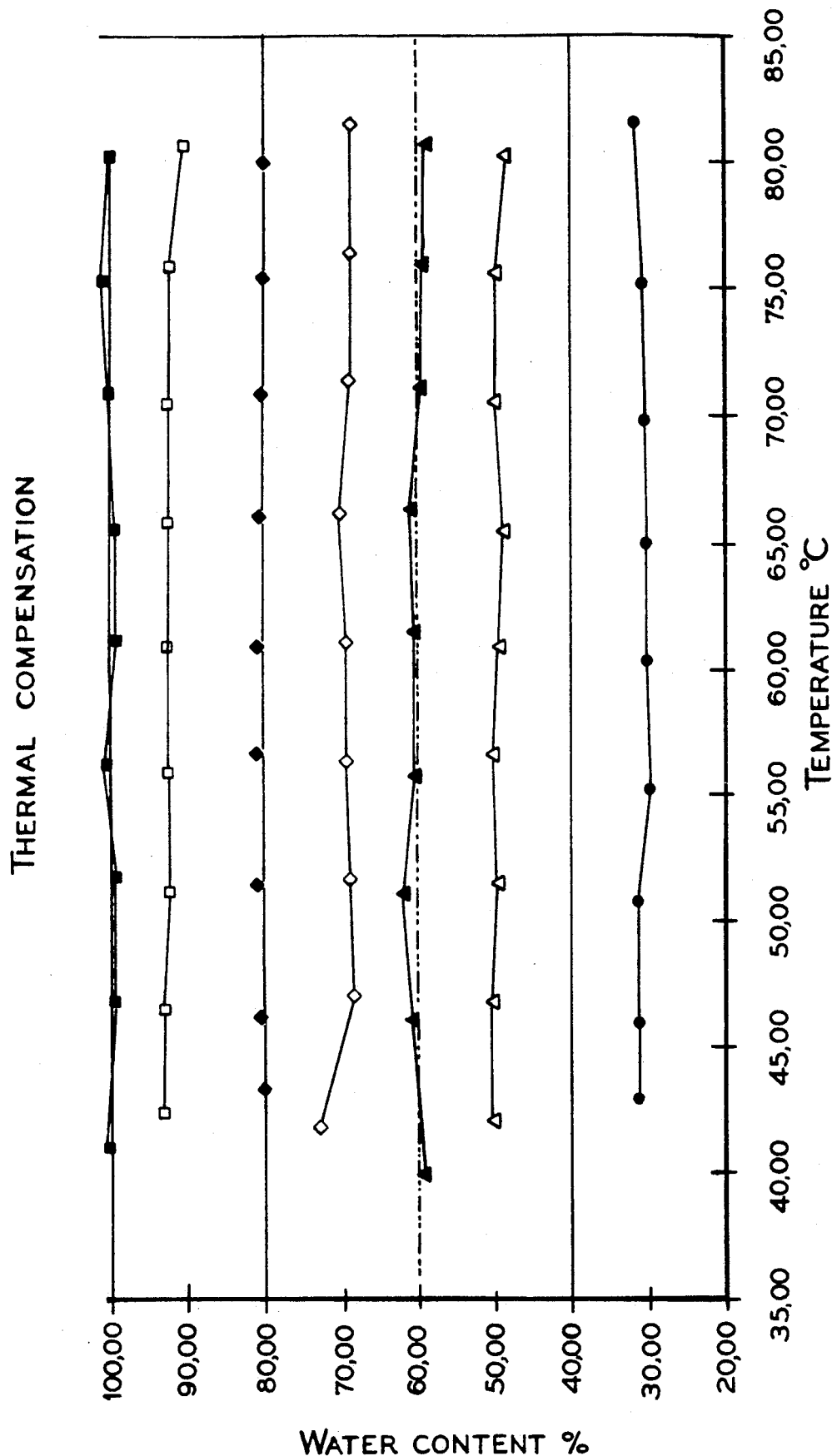

METHOD AND APPARATUS FOR DETERMINING THE PERCENTAGE WATER CONDENT OF OIL IN WATER EMULSION BY SPECIFIC ADMITTANCE MEASUREMENT

BACKGROUND OF THE INVENTION

The present invention relates to an apparatus and a method for measuring the percentage content of one constituent of a two component fluid mixture. The method and apparatus of the present invention have particular utility in measuring the percentage water content in an oil-in-water emulsion in which the continuous phase is water flowing through an oil pipeline.

Oil-in-water emulsions are commonly employed in the transportation of oil. When using these emulsions, it is beneficial to know the percentage water content of the emulsion. A variety of different techniques have been employed to measure the water content.

In one approach, a percentage water measuring circuit is employed which has a capacitance probe for measuring the specific capacitance of the oil-in-water emulsion. The circuit further includes a reference capacitor of known value in series with the capacitance probe, a variable gain alternating-current voltage generator connected in series with the reference capacitor and the capacitance probe for applying an alternating-current voltage across each, a voltage measuring circuit for measuring the actual voltage differential across the probe, an error detecting circuit for detecting the difference between the actual voltage differential across the capacitance probe and a predetermined voltage, a voltage measuring circuit for obtaining the voltage differential appearing across the reference capacitor and a non-linear to linear function generator to convert the voltage differential to a linear function with respect to the percentage water content. A system employing this type of circuit is shown in U.S. Pat. No. 3,768,006 to Mueller.

The primary deficiency of this approach has been the complexity of the circuitry involved. Additionally, questions have been raised as to the accuracy of the measurements.

Other approaches to determining the water content in oil are shown in U.S. Pat. Nos. 4,240,028 to Davis, Jr., 4,289,020 to Paap, 4,429,273 to Mazzagatti and 4,820,970 to Swanson. The Davis, Jr. patent is directed to an apparatus which includes a sensor spacially arranged within a pipe for providing a signal whose frequency and amplitude corresponds to the water saturation. The sensor senses capacitance changes in the oil-in-water emulsion flowing through the pipe. A circuit connected to the sensor provides a signal corresponding to the difference between the sensor signal and a reference signal established for a 100% water saturation. The water content is determined from this difference signal.

The Paap patent relates to a microwave-gamma ray water-in-crude monitor. A microwave transmitter and a gamma ray source are arranged with a measuring cell through which crude oil flows and are used to transmit microwave energy and gamma rays through the cell. A microwave receiver and a gamma ray detector receive the energies transmitted through the measuring cell and provides signals in accordance with the received energies. Apparatus connected to the microwave receiver and to the gamma ray detector provide a display of the water content of the crude oil in accordance with the signals from the microwave receiver and the gamma ray detector.

The Mazzagatti patent relates to an oil-in-water monitor which includes a test cell having a production stream passing through it so as to allow the dielectric properties of the production stream to be monitored. An analyzer connected to the measuring cell provides an indication of the water content of the production stream in accordance with the dielectric properties of the production stream.

The Swanson patent relates to a microwave system for determining the volume fraction of water in a fluid. A microwave beam having a frequency which varies with time is transmitted through the liquid and absorption losses are calculated. The volume fraction of water is determined according to the absorption losses.

These additional techniques have not significantly improved the measurement of the percentage water content of an oil-in-water emulsion.

SUMMARY OF THE INVENTION

Accordingly, it is an object of the present invention to provide an apparatus and method for measuring the percentage content of the constituents in a two component fluid system.

It is a further object of the present invention to provide an apparatus and method which easily makes quantitative determinations of the percentage water content of a fluid system.

It is yet a further object of the present invention to provide a method and apparatus as above which readily determines the percentage water content of an oil-in-water emulsion.

These and other objects and advantages will become more apparent from the following description and drawings in which like reference numerals depict like elements.

The foregoing objects are achieved by the apparatus and method of the present invention. While the apparatus and method of the present invention have broad applicability, they will be described in the context of a system for determining the water content in an oil-in-water emulsion. The apparatus broadly comprises a sensor for measuring the real part of specific electrical admittance of a fluid system such as an oil-in-water emulsion flowing through a conduit or pipeline, means for adjusting the measured real part of specific admittance to the temperature of the system flowing through the conduit, and means for converting the adjusted measured real part of specific admittance into an electrical current signal representative of the percentage water content of the system. The adjusting means comprises a temperature compensation device and an electrical circuit for producing a temperature adjusted signal representative of the water content.

In a first embodiment of the apparatus, the temperature compensation device comprises a temperature sensor having an RTD (Resistance Temperature Detector) mounted within a housing placed in contact with the oil-in-water emulsion flowing through the conduit. The RTD is fed with a constant current source and the voltage across the resistance is measured. This voltage signal is representative of the emulsion temperature. The signal is provided to a processor for producing the adjusted signal representative of the water content.

In a second embodiment of the present invention, the temperature compensation device comprises an electrode submerged in a reference water sample. A container with the electrode and the water sample are immersed in the oil-in-water emulsion flow so that the reference water sample is at the same temperature as the emulsion flows through the pipeline. A reference voltage signal representing the real part of specific admittance of 100% water at the temperature of the emulsion is provided to a processor for adjusting the measured emulsion real part of specific admittance signal with respect to temperature.

The sensor for measuring the real part of specific admittance of the emulsion preferably is immersed or submerged within the oil-in-water emulsion. The sensor comprises two spaced apart electrodes and an intermediate dielectric layer (used only as a support element).

The method of the present invention broadly comprises measuring the real part of electrical specific admittance of an oil-in-water emulsion flowing through a conduit and providing a signal representative thereof, providing a reference signal indicative of the emulsion temperature, adjusting said measured signal with said reference signal, and converting said adjusted signal into a current signal representative of the percentage water content of the emulsion.

Further details of the present invention will be described in the following description and the drawings.

BRIEF DESCRIPTION OF THE DRAWINGS

FIG. 6 shows the thermal compensation of the sensor.

DETAILED DESCRIPTION

Figure 1:
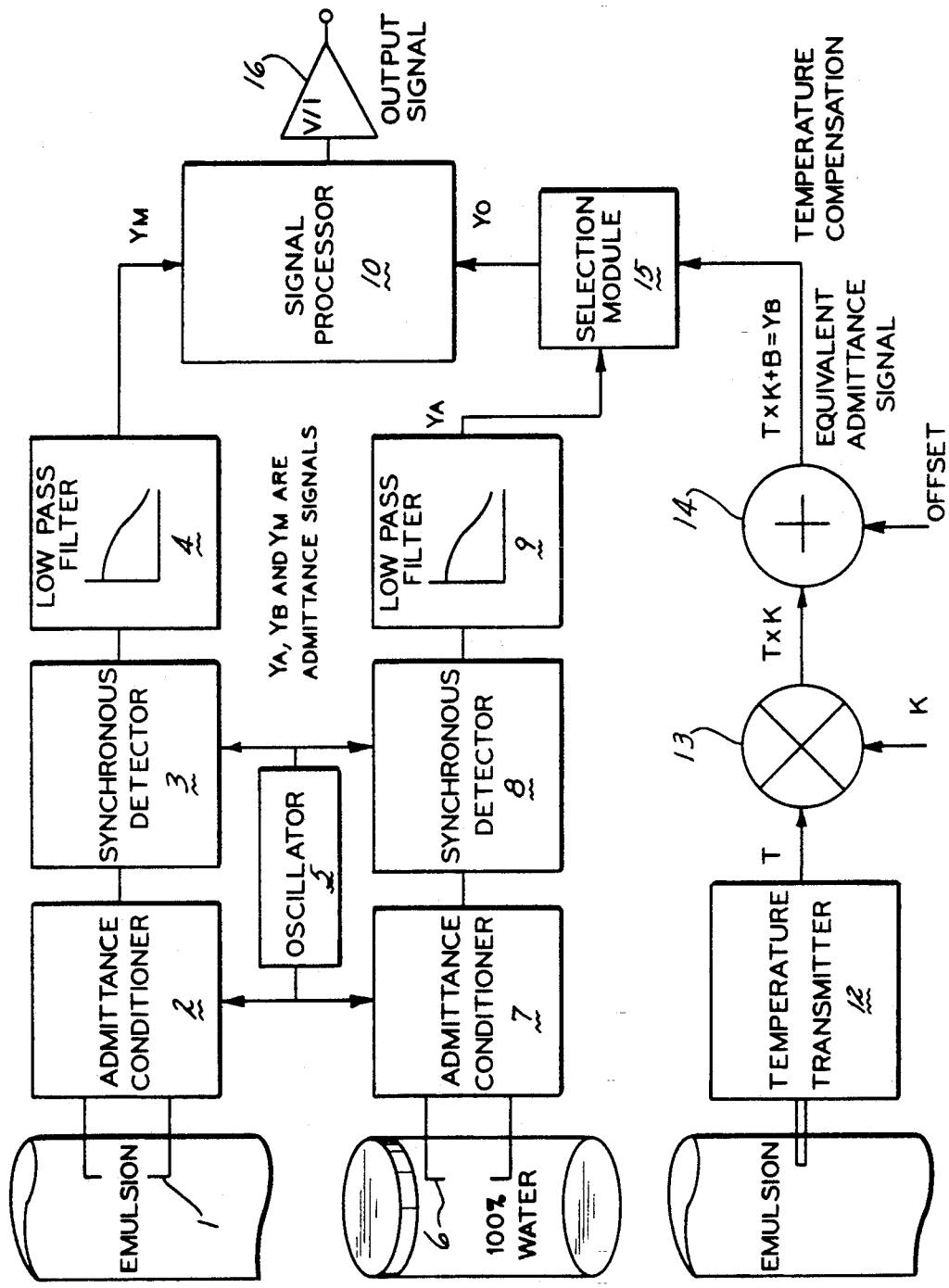
FIG. 1 shows a conceptual block diagram of the sensor.

FIG. 1 is a conceptual block diagram of the sensor. A pair of electrodes 1 submerged in the emulsion are excited by an admittance conditioner 2 with a frequency of 100 Khz by oscillator 5. At this frequency the polarization resistance is eliminated. The polarization resistance is an increase of the electrodes resistance due to the formation of emulsion film layers on the surface of said electrodes. With the use of the aforementioned frequency the polarization resistance is decreased considerably. The output signal of admittance conditioner 2 is detected synchronically by detector 3 and filtered by low pass filter 4. This signal (Ym) from filter 4 is representative of the real part of the specific admittance of the emulsion. Similarly, a pair of electrodes 6 identical to electrodes used in the oil-in-water emulsion are submerged in 100% reference water. The reference water is in thermal contact with the emulsion. The electrodes 6 are excited by admittance conditioner 7 in the same manner described above with regard to electrodes 1. The output signal is processed by detector 8 and filter 9. In this case, the output from filter 9 (Ya) is representative of the real part of the specific admittance of 100% reference water. An RTD transmitter 12 is in thermal contact with the emulsion and produces a signal representative of the temperature of the emulsion. This signal is linearly scaled by blocks 13 and 14 according to a previous calibration with the 100% reference water and the scaling is adjusted so as to obtain an equality in signals between Yb and Ya. A switch on selection module 15 selects either a signal representative of the real part of the specific admittance of 100% reference water or the equivalent signal obtained by processing the simple emulsion temperature by the components 12, 13 and 14. The signal processor 10 receives two signals Yo and Ym, and generates an output signal that is representative of the water content of the emulsion independent of any temperature change, as will be discussed hereinafter. The circuit further includes a voltage-to-current converter 16 for converting the voltage output signal from processor 10 to a current output signal having a current value in the range of from about 4 mA to about 20 mA.

Figure 2:
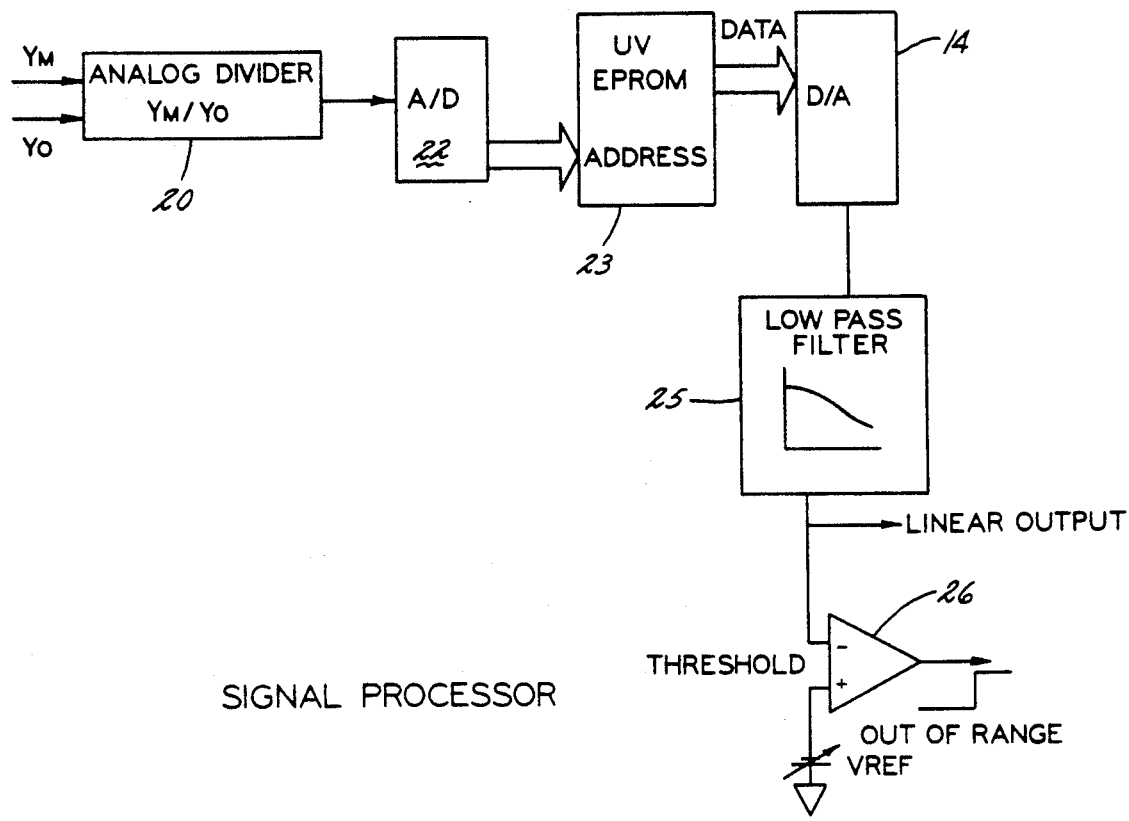
FIG. 2 is a description of the signal processor.

FIG. 2 is a block diagram of the signal processor 10. The processor 10 includes an analog divider chip 20 having as inputs Ym and Yo and having Ym/Yo as output. Convertor 22 converts the output signal into a digital binary code. This binary code is used as an address to access the data recorded on the UV EPROM 23 (Ultraviolet Eraseable Programmable Read Only Memory). The data values of the UV EPROM 13 (calculated from equation No. 3 hereinbelow) corresponds to the content of water in the emulsion. These data values are converted from digital to analog signal converter 24 and low pass filter 5 smooths that signal to obtain a voltage representative of the content of water in the emulsion. In order to prevent an out of range measurement, detector 26 detects the minimum practical threshold. The value of the threshold is selected according to the sensibility of the system or to the possible inversion of the emulsion.

Figure 3:
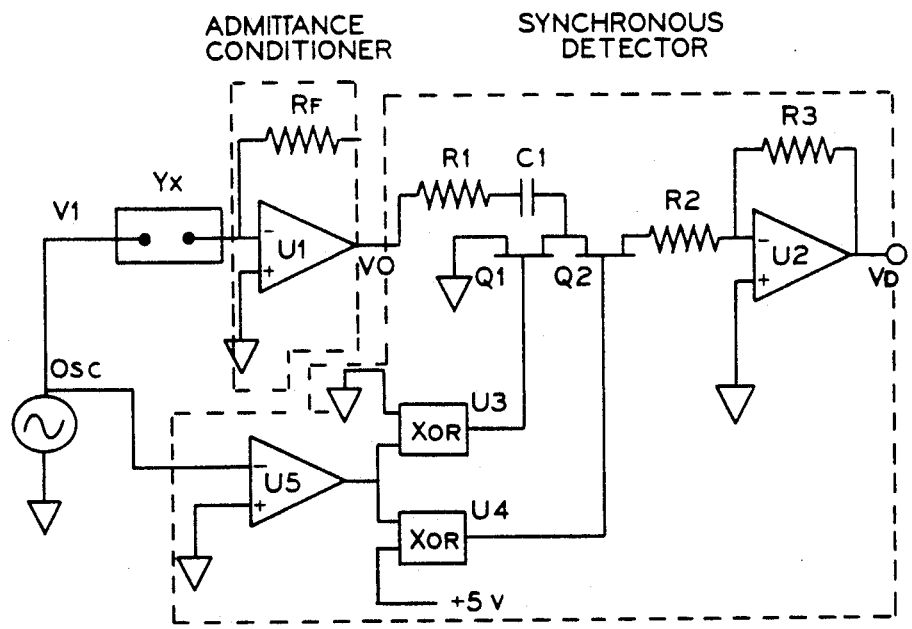
FIG. 3 shows details for the admittance conditioner and the synchronous detector.

FIG. 3 describes the electrical details of elements 2 or 7 and 3 or 8. The admittance conditioner is just an operational amplifier that provides an output Vo proportional in amplitude to the admittance of the electrodes submerged in the oil-in-water emulsion or 100% reference water (see FIG. 1) and a resistance value Rf, which is used to select the scale range. The signal Vo is processed by the quadrature detector to obtain the real part of a signal proportional to the admittance. This is accomplished at multiplying the signal Vo by unitary pulse with Q1 and Q2 where the pulse is provided by U3 and U4. U5 is a comparator that squares the oscillator sinewave.

Figure 4:
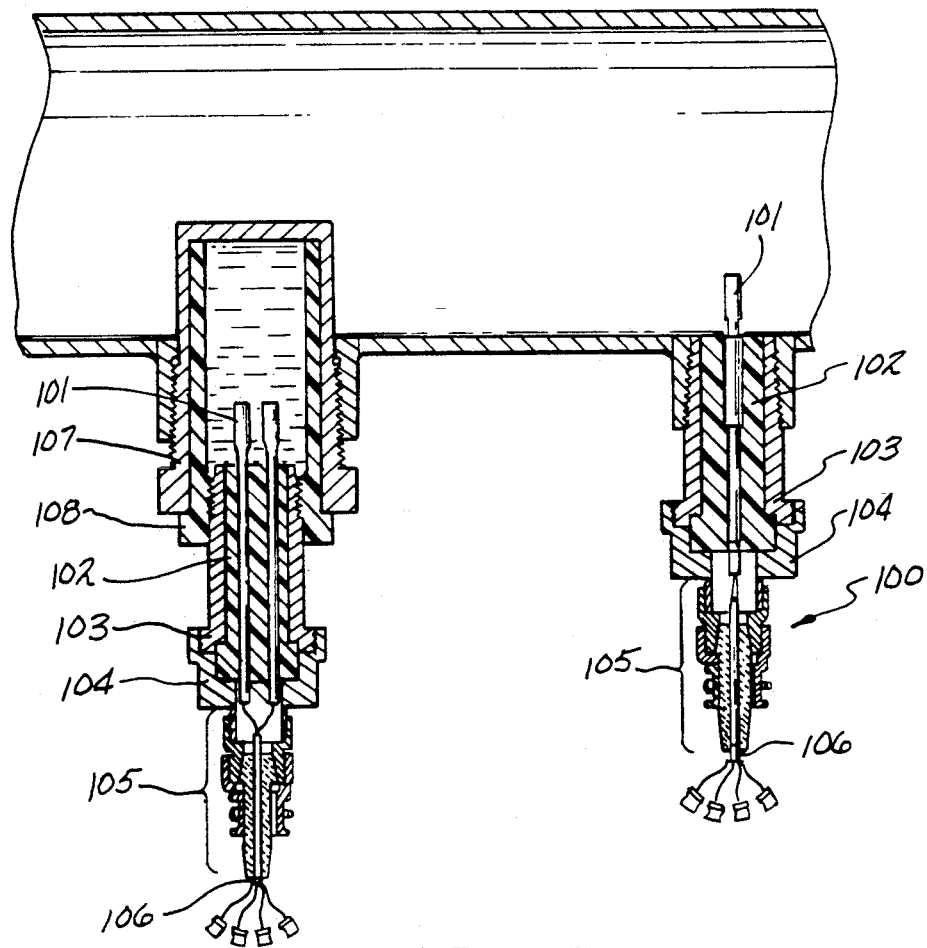
FIG. 4 is a partial sectional view of a pipeline provided with a sensor for measuring the percentage water content of the oil-in-water emulsion flowing therethrough.

FIG. 4 illustrates a portion of a conduit or pipeline through which an oil-in-water emulsion is flowing. The water in the emulsion is a highly conductive component, while the crude oil therein is a highly non-conductive component. Therefore, the conductivity of the emulsion increases as the percentage water content increases. The emulsion real part of specific admittance measuring sensor 100 used in the apparatus of the present invention comprises electrodes 101 made out of stainless steel. The electrodes are secured to a body 102 made out of teflon which functions to electrically isolate the electrodes 101 from the production pipeline thereby eliminating in any way grounding problems. Body 102 is fixed in a connection 103 which allows it to be installed in the production pipeline by 1" NPT thread. Cap 104 is screwed to connection 103 and functions to protect the connection between electrodes 101 and coaxial cable 106. A cap 104 compresses the body 102 against the pressure of the production pipeline.

Cableholder 105 prevents the rupture of connection between cable 106 and electrode 101.

The water admittance measuring sensor 110 is constructed in a similar manner as sensor 100 and, therefore, like reference numerals connote like elements. In addition, sensor 110 includes piece 107 which is made out of stainless steel having a 2" NPT male thread allowing the connection of the ensemble to the production pipeline. A piece 108 is a teflon element within 107 which defines therewith a water compartment.

The teflon cover electrically isolates the measurement electrodes 101 and this avoids electrical conduction between measurement electrodes and the piece 107. However, the presence of water in the container creates a finite conductivity between the bottom of piece 107 and the measurement electrodes. On the other hand, in order to reduce this influence the design is made so that the distance between the electrodes and the bottom of the piece 107 is six times larger than the distance between the measurement electrodes.

Figure 5:
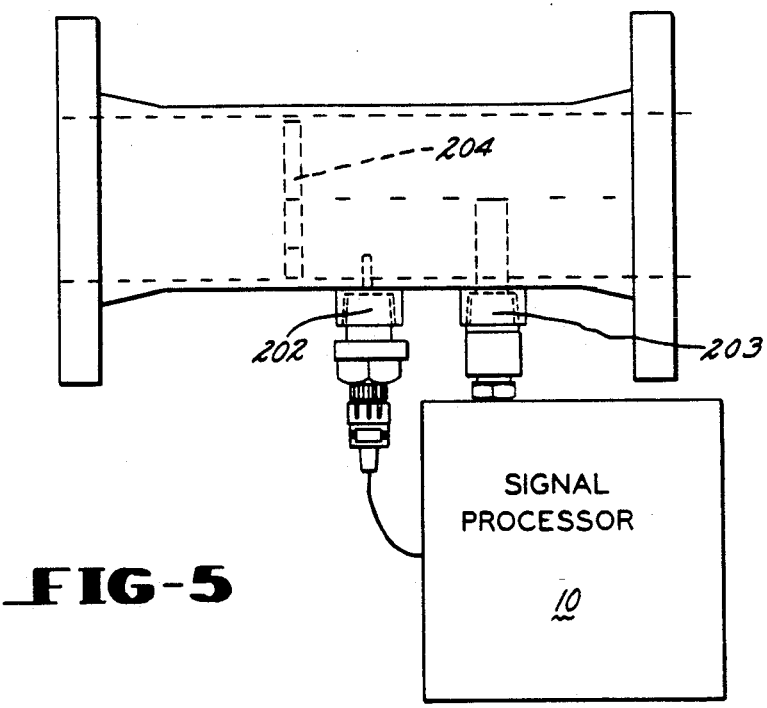
FIG. 5 is a partial sectional view of an alternative embodiment of the present invention.

FIG. 5 illustrates an alternative system for measuring the percentage of water content of an emulsion. In this system an admittance sensor 202 identical to that shown in FIG. 4 is again submerged in a two component liquid as an oil-in-water emulsion. The system differs from that shown in FIG. 4 in that temperature compensation is made differently. The temperature sensor 203 comprises an RTD fixed within a thermowell casing. The RTD may be a PT100 that behaves according to the equation $Rt = Ro(1+\alpha t)$, where $Ro$ = resistance in $\Omega$ at 0° C., $Rt$ = Resistance in $\Omega$ at t° C., $\alpha$ = temperature coefficient = $0,00392\Omega/\Omega$ ° C., t = temperature in ° C. A signal processor of the type described in FIGS. 1 and 2 is mounted in a box 4 near to the electrodes of the sensor. A variable plate orifice 204 is employed in the pipeline to improve the mixing of the water and crude oil.

FIG. 6 shows the thermal compensation of the sensor of the present invention. A sample preparation is made mixing crude oil previously centrifugated with less than 1% of water content. A nonionic surfactant INSTANT 100 TM is used in order to stabilize the emulsion in a large range of water concentrations. Samples with water concentrations from 30% to 100% at 10% increments were made. The thermal compensation is made from about 40° C. to about 80° C. The stability of the thermal bath is lower than 0.1° C. 30 minutes is taken for temperature stabilization in each point. The temperature transmitter is a Rosemount programmable "Smart Transmitter" model 3044 for RTD with a precision of 0.14° C. The voltage applied to the sample is of the order of 1 volt.

Figure 7:
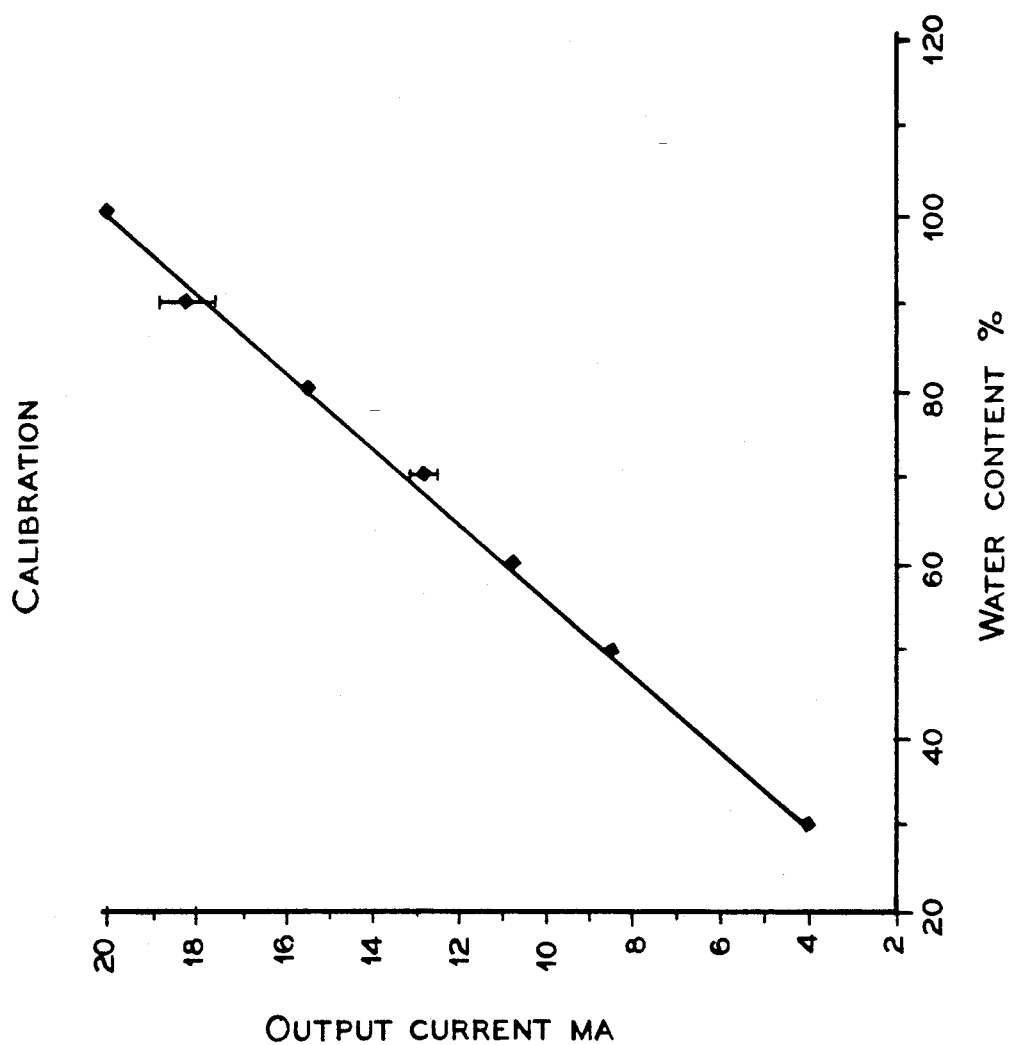
FIG. 7 is a calibration curve of percent water content vs. current.

FIG. 7 is a calibration of water content vs. current using the same experiment described in FIG. 6 but restricted to a single temperature of 60° C. and reading the corresponding current at the output signal terminal 16 of FIG. 1.

The principles upon which the system shown in the FIGURES is based can be expressed in the following manner. The admittance $\Lambda m$ of the oil-in-water emulsion can be expressed by the following equations:

$$\Lambda m = \frac{\Lambda 1 (1 + 2s)}{1 - s}, \text{ where } s = \frac{V2(\Lambda 2 - \Lambda 1)}{2\Lambda 1 + \Lambda 2}$$

$V2$ = Fraction of disperse phase 2
$\Lambda 1$ = Specific admittance of continuated matrix 1
$\Lambda 2$ = Specific admittance of disperse phase 2

This expression is completely general and independent of which phase is either continuated or dispersed (oil or water). For the special case of phase 1 water and phase 2 crude oil, $\Lambda 2 \leqq \Lambda 1$ and the approximation $\Lambda 2 = 0$ is quite good. In this case:

$$\Lambda m = \frac{2 \times \Lambda 1}{3 - x}, \text{ where } x = 1 - V2.$$

This relation is also valid for the real and imaginary part of the specific admittance.

In the description of the signal processor shown in FIG. 2 the uv EPROM lockup table is precisely the inverse of equation 3 but applied to the real part of the specific admittance:

$$x = \frac{3Re(\Lambda m)/Re(\Lambda 1)}{2 + Re(\Lambda m)/Re(\Lambda 1)}$$

where $\Lambda m$ corresponds to Ym, $\sqrt{1}$ correspond to Yo.

The idea behind using equation 3 for temperature compensation lies in the fact that the temperature dependence of the oil-in-water emulsion admittance $\Lambda m$ is due to the temperature dependence of $\Lambda 1$. Then the ratio $\Lambda m/\Lambda 1$ is independent of temperature and is function only of the content of water of the emulsion. This property is used in the option that use the 100% water sample. In this case $\Lambda 1$ corresponds to the admittance of the 100% water sample. In the case of temperature compensation using the RTD, a signal equivalent to the admittance $\Lambda 1$ is generated so that, to the signal processor, no difference is felt between the RTD and the admittance measurement. If the conductivity of the water is due to strong electrolites both methods are equivalent because the temperature dependence of the admittance is linear in a large range of temperature. For weak electrolites such is not the case and the 100% water sample option must be used. This option is valid no matter which is the electrolite composition of the water.

As can be seen from the foregoing description, the present invention provides an easy way to make quantitative determinations of emulsified water in crude oil. It provides the advantages that it solves simultaneously the non-linearity of the response and the temperature compensation.

While the invention has been described in the context of determining the water content of an oil-in-water emulsion, it can be used to detect quantities of particular fluids in two component systems as long as the fluids have different conductivities from one another. For example, the present invention could be used in the food industry to determine the water proportion in liquid foods.

The present invention is advantageous in that it has applicability in oil-in-water separators to obtain optimal control and in monitoring crude oil loads in tankers or other transport systems.

It is apparent that there has been provided in accordance with this invention a system and method for measuring crude oil-in-water percentages which fully satisfies the objects, means, and advantages set forth hereinbefore. While the invention has been described in combination with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

What is claimed is:

1. An apparatus for measuring the percentage water content of an oil-in-water emulsion which comprises:
   means for measuring the real part of specific admittance of an oil-in-water emulsion flowing through a conduit and providing a signal representative of said measured real part of specific admittance;
   means for adjusting said measured real part of specific admittance in response to the temperature of said emulsion flowing through said conduit and forming a signal representative thereof; and
   means for converting said adjusted measured real part of specific admittance signal into an electrical signal representative of the percentage water content of said emulsion.

2. The apparatus of claim 1 further comprising:
   said measuring means including a sensor submerged in said emulsion; and
   said sensor including two electrodes separated by a dielectric material for producing a voltage signal representative of the real part of specific admittance of said emulsion.

3. The apparatus of claim 2 further comprising:
   means for applying an alternating current having a frequency of at least about 100 KHz to said electrodes.

4. The apparatus of claim 2 wherein said adjusting means includes a sensor for measuring the temperature of said emulsion.

5. The apparatus of claim 4 wherein said temperature sensor comprises an outer housing in contact with said emulsion, an inner housing in contact with said outer housing, and a temperature detector mounted within a thermo well, whereby said sensor produces a voltage signal representative of said temperature of said emulsion.

6. The apparatus of claim 5 further comprising:
   means for obtaining an amplified voltage signal by a synchronous detector representative of said measured real part of specific admittance;
   said adjusting means further including means for processing said amplified voltage signal to produce a voltage signal representative of said adjusted real part of specific admittance; and
   said processing means receiving said voltage signal representative of said temperature as an input.

7. The apparatus of claim 6 wherein said converting means comprises a voltage-to-current converter for converting said voltage signal representative of said adjusted real part of specific admittance to a standard output current.

8. The apparatus of claim 2 wherein said adjusting means comprises:
   a reference sample of the water contained in said emulsion;
   said water sample being in contact with the oil-in-water emulsion so as to be at the same temperature as said emulsion; and
   two electrodes submerged in said water sample for producing a reference voltage signal representative of the real part of specific admittance of said 100% water sample.

9. The apparatus of claim 8 wherein said adjusting means further comprises:
   means for obtaining an amplified voltage signal representative of real part of specific admittance of said emulsion and said reference water sample; and
   means for processing said signals to form voltage signal representative of adjusted real part of specific admittance.

10. The apparatus of claim 9 wherein said converting means comprises a voltage-to-current converter for converting said adjusted impedance voltage signal to a current outlet signal having a current value in the range of from about 4 mA to about 20 mA.

11. An apparatus for measuring the percentage content of the respective components of a two component liquid system, said apparatus comprising
    means for measuring real part of specific admittance of said liquid system and for providing a first electrical signal representative of said measured real part of specific admittance;
    means for producing a reference signal related to the temperature of said liquid system;
    means for modifying said first signal with said reference signal to compensate for temperature induced effects upon the measured real part of specific admittance; and
    means for converting said modified signal into a current signal representative of percentage content of one component of said system.

12. A method for measuring the percentage water content of an oil-in-water emulsion flowing through a pipeline, said method comprising:
    measuring the real part of specific admittance of said oil-in-water emulsion flowing through said pipeline and providing a first signal representative of said measured real part of specific admittance;
    providing a reference signal indicative of emulsion temperature;
    adjusting said first signal with said reference signal so as to compensate for temperature effects; and
    converting said adjusted first signal to a current signal representative of the percentage water content of said emulsion.

13. The method of claim 12 wherein said reference signal providing step comprises:
    measuring said emulsion temperature with a temperature detector; and
    produce a voltage signal representative of said measured temperature.

14. The method of claim 12 wherein said reference signal providing step comprises:
    placing a sample of said water in said emulsion in contact with said emulsion so that said sample is at the same temperature as said emulsion;
    measuring the real part of specific admittance of said water sample; and
    providing a voltage signal representative of said measured water real part of specific admittance.

* * * * *